United States Patent [19]

O'Lenick, Jr. et al.

[11] Patent Number: 5,733,533
[45] Date of Patent: Mar. 31, 1998

[54] RECONSTITUTED SILICONE WAX ESTERS

[75] Inventors: Anthony J. O'Lenick, Jr., Lilburn, Ga.; Carter La Vay, Riverside, Conn.

[73] Assignees: Lambent Technologies Inc., Norcross, Ga.; J.W. Hanson Co., Woodbury, N.Y.

[21] Appl. No.: 882,487

[22] Filed: Jun. 25, 1997

[51] Int. Cl.$^6$ .............................. A61K 7/027; C07F 7/10; C07F 7/08; C07F 7/18

[52] U.S. Cl. ............... 424/64; 554/77; 556/437; 556/440

[58] Field of Search ............... 554/77; 556/437, 556/440; 424/64

[56] References Cited

U.S. PATENT DOCUMENTS

| | | | |
|---|---|---|---|
| 5,180,843 | 1/1993 | O'Lenick | 556/77 |
| 5,446,184 | 8/1995 | O'Lenick | 556/437 |

*Primary Examiner*—C. Warren Ivy
*Assistant Examiner*—Evelyn Huang

[57] ABSTRACT

The present invention relates to certain reconstituted wax esters, prepared by the reaction of a silicone polymer and a natural high molecular wax ester selected from the group consisting of beeswax, candelillia, and carnauba wax. These materials are useful in preparation of cosmetic products where their ability to couple organic silicone and other components into a uniform mass is unsurpassed. One major area for the use of these materials is in lipsticks. In addition they are useful in antiperspirants and other formulations which contain both oils and silicones.

14 Claims, No Drawings

RECONSTITUTED SILICONE WAX ESTERS

TECHNICAL FIELD

The present invention relates to certain reconstituted wax esters, prepared by the reaction of a silicone polymer and a natural high molecular wax ester selected from the group consisting of beeswax, candelillia, and carnauba wax. These materials are useful in preparation of cosmetic products where their ability to couple organic, silicone and other components into a uniform mass is unsurpassed. One major area for the use of these materials is in lipsticks. In addition they are useful in antiperspirants and other formulations which contain both oils and silicones.

BACKGROUND OF THE INVENTION

The present invention relates to compositions which result from the transesterification of a wax ester and any hydroxyl containing silicone compound. Waxy esters derived from the reaction of a fatty acid and hydroxy silicone are known. U.S. Pat. No. 5,180,843 to O'Lenick, (January 1992) teaches that fatty acids, and triglycerides can be reacted with hydroxy containing silicone compounds to form esters. The products of the referenced O'Lenick patent are different in several regards than the compounds of the present invention. Specifically, the O'Lenick patented products are made from fatty acids, triglycerides or fatty methyl esters. The by product of such a reaction is water, glycerin, or methanol respectively. As will become clear from reading the disclosure of the present invention, the compounds of the present invention are made by reacting a specific type wax ester which has a long chain acyl moiety, and a long chain alcohol moiety in the ester. The reaction of such a material with a hydroxy silicone results in a "reconstituted" as indicated by the following reaction:

$$R^1-C(O)-OR^2 + \text{Silicone-OH} \rightarrow R^1-C(O)-O\text{-Silicone} + R^2OH.$$

We have surprisingly found that the silicone ester in presence of the $R^2OH$ in the reaction mixture, results in enhanced solubility, compatability and emuslifiability of the product.

OBJECT OF THE INVENTION

It is the object of the present invention to provide unique compositions which have an ability to solubilize or couple silicone compounds and fatty compounds.

DETAILED DESCRIPTION OF THE INVENTION

Beeswax, carnauba wax and candelilla wax contain natural esters, which conform to the following structure:

$$R^1C(O)O-R^2$$

wherein:

$R^1$ is alkyl having 19 to 37 carbon atoms, $R^2$ is alkyl having 20 to 38 carbon atoms.

The relatively high number of carbon atoms in the compounds is one factor which makes these waxes somewhat unique, compared to oils like tallow, coconut oil, and soybean oil. This higher molecular weight and the fact that it causes the product to be solid makes results in the classification of these compounds as waxes, rather than oils. The term oil is applied to liquid products.

Silicone and aliphatic compounds like waxes are mutually immicible in each other, resulting in a two phase system. It has been a long felt need to be able to formulate a product in which silicone and waxes are in one phase, uniformly distributed. The compounds of the present invention address this problem.

It should be clear from the reaction sequence that the hydroxy silicone is "reconstituted" into the ester, making a new silicone ester and leaving a free alkyl alcohol (the $R^2OH$), reacted from the starting wax. The resulting composition contains a silicone alkyl ester and an alcohol which is derived from the original wax. This combination is an excellent coupler, solubilized and emulsifier for placing the starting wax and silicone in a uniform product. This is very important in a variety of applications, like automotive polishes, and personal care products like lipsticks.

The compositions of the present invention comprise:

a) a silicone ester conforming to the following structure

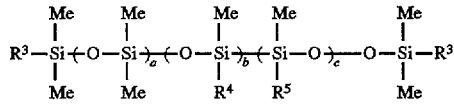

wherein:

Me is methyl;

a is an integer ranging from 0 to 2000;

b is an integer ranging from 1 to 20;

c is an integer ranging from 0 to 20;

$R^3$ is Me or $-(CH_2)_3-O-(CH_2CH_2O)_x-(CH_2CH(CH_3)O)_y-(CH_2CH_2O)_z-C(O)R^1$ $R^4$ is Me or $-(CH_2)_3-O-(CH_2CH_2O)_x-(CH_2CH(CH_3)O)_y-(CH_2CH_2O)_z-C(O)R^1$, each of x, y, z is an integer ranging from 0 to 20, with the proviso that both $R^3$ and $R^4$ cannot be Me at the same time;

$R^5$ is $-(CH_2)_n-CH_3$;

n is an integer ranging from 1 to 17;

$R^1$ is alkyl having 19 to 37 carbon atoms. and b) a hydroxy compound conforming to the following structure:

$$R^2-OH$$

wherein;

$R^2$ is alkyl having 20 to 38 carbon atoms.

In a preferred embodiment the concentration of the hydroxy compound ranges from 1 to 10% by weight.

In another preferred embodiment the concentration of the hydroxy compound ranges from 5 to 10% by weight.

In another preferred embodiment n is an integer ranging from 11 to 17.

In a preferred embodiment a is an integer ranging from 10 to 50.

In another preferred emboodiment a is an integer ranging from 15 to 25.

In another preferred embodiment c is 0.

In still another preferred embodiment c is an integer ranging from 1 to 10.

In another preferred embodiment c is an integer ranging from 1 to 5.

In addition the compositions of the present invention are made by the esterification reaction of a silicone compound conforming to the following structure:

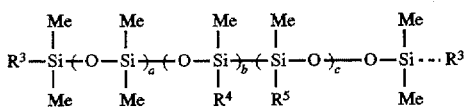

wherein:

Me is methyl;

a is an integer ranging from 0 to 2000;

b is an integer ranging from 1 to 20;

c is an integer ranging from 0 to 20;

$R^3$ is Me or —$(CH_2)_3$—O—$(CH_2CH_2O)_x$—$(CH_2CH(CH_3)O)_y$—$(CH_2CH_2O)_z$—H $R^4$ is Me or —$(CH_2)_3$—O—$(CH_2CH_2O)_x$—$(CH_2CH(CH_3)O)_y$—$(CH_2CH_2O)_z$—H, each of x, y, z is an integer ranging from 0 to 20, with the proviso that both $R^3$ and $R^4$ cannot be Me at the same time;

$R^5$ is —$(CH_2)_n$—$CH_3$;

n is an integer ranging from 1 to 17; and a wax selected from the group consisting of beeswax, carnauba wax and candelillia wax.

In a preferred embodiment said wax is beeswax.

In another preffered embodiment said wax is carnauba.

In still another preffered embodiment said wax is candelillia wax.

In a preffered embodiment said reaction is carried out at a temperature of between 180 and 200 C.

Waxes

The waxes useful as raw materials in the preparation of the compositions of the present invention are commercially available from J. W. Hanson Company Inc. Woodbury, N.Y.

Beeswax

Beeswax, which is also known as white wax, is an insect wax cultured worldwide; it is found on all continents of the globe. The chemical composition of the wax varies slightly depending upon the specie of the bee producing the wax. To extract the beeswax for use the honeycomb is melted or boiled with water and the crude wax is skimmed off the top. The color of the crude material is dependent upon the type of flower producing the pollen and the age of the hive. Natural waxes of animal origin are complex in structure and as such, possess unique properties which render then invaluable raw material for many of today's industries.

Natural Beeswax is amorphid and varies in color from a deep brown to a light taffy shade. The wax has a distinctive honey odor. Beeswax has a melting point of between 62–65 C. It's CAS number is #8006-40-4.

Carnuba Wax

Currently, the only place in the world where the Carnauba Palm tree can be found is in northeastern Brazil. This Palm tree (Capernicea cerifera), often called the "tree of life," produces a wax on its leaves, protecting them from the severe weather conditions of the area. Harvesting occurs around September following traditional procedures, the leaves are cut and are laid on the ground to dry in the sun. Modern technology takes over to scrape this valued product from its leaf. Two types of wax are obtained, one pure and clear from the center of unopened leaves, called yellow grade wax; the second from the leaf itself called gray powder.

Carnauba Wax is an environmentally correct natural raw material and is the hardest of the natural waxes. In addition, it has the highest melting point of waxes and is brittle and nontacky. Carnauba possesses excellent gelling properties, is emulsifiable and also has the ability of retaining oil. These properties assure its premiere position in the global market place, for food, pharmaceutical, and advanced technologies.

Carnauba Wax is a hard, brittle, non-tacky and lustrous wax, having a melting point of between 83.0–86 C. It's CAS number is 8015-86-9.

Candelillia Wax

Candelillia Wax is extracted from the outer surface of Candelilla plants, which are native to the arid regions of Northern Mexico. The plants grow wild in the plains and in the foothills of Mexico's North-Central plateau. With a melting point ranging from 66 to 71 C., candellillia is well suited to the preparation of many wax products where resistance to heat is an important consideration. Candelilla wax is used in polishes dressings, coatings, and finishes, where a reasonably high melting point is desirable. In addition, this wax blends easily with fatty acids, paraffin, and other waxes used in the manufacture of candles and tapers. Candellillia can be used for dyes in the printing of various materials providing excellent lubricant properties and resistance to high pressure.

Candelillia is a light brown to light yellow, hard, brittle, slightly tack and lustrous wax with a distinctive odor. This wax is not as hard as Carnuba and does not reach its maximum hardness until several days after cooling. It has a melting point of between 68.5–72.5

Carnuba, beeswax and candellillia wax are soluble in vegetable and animal waxes and a large variety of natural and synthetic resins as well as fatty acids, glycerides, and hydrocarbons. They are insoluble in silicone. The waxes are esters having between 20 and 38 carbon atoms in the chain. This unique carbon distribution gives the compatibilizes fatty oils and waxes with silicone oills. This is highly desirable in the personal care applications like lipsticks and antiperspirant applications. The hydroxy compound, produced as a by product of the reaction is a co-solubilizer, likewise have between 28 and 37 carbon atoms and the presence of the hydroxy compound helps significantly in the compatibilization of waxes and oils in silicone.

Silicone Compounds

The silicone compounds useful as raw material in the preparation of the compositions of the present invention conform to the following structure:

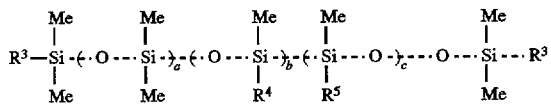

wherein:

Me is methyl;

a is an integer ranging from 0 to 2000;

b is an integer ranging from 1 to 20;

c is an integer ranging from 0 to 20;

$R^3$ is Me or —$(CH_2)_3$—O—$(CH_2CH_2O)_x$—$(CH_2CH(CH_3)O)_y$—$(CH_2CH_2O)_z$—H;

$R^4$ is Me or —$(CH_2)_3$—O—$(CH_2CH_2O)_x$—$(CH_2CH(CH_3)O)_y$—$(CH_2CH_2O)_z$—H, with the proviso that both $R^3$ and $R^4$ cannot be Me at the same time;

$R^5$ is —$(CH_2)_n$—$CH_3$;

n is an integer ranging from 1 to 17.

Compounds of this type are commercially available from Siltech Inc. Norcross, Ga.

The compositions of the present invention comprise:

a) a silicone ester conforming to the following structure

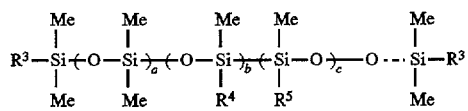

wherein:

Me is methyl;

a is an integer ranging from 0 to 2000;

b is an integer ranging from 1 to 20;

c is an integer ranging from 0 to 20;

$R^3$ is Me or $-(CH_2)_3-O-(CH_2CH_2O)_x-(CH_2CH(CH_3)O)_y-(CH_2CH_2O)_z-C(O)R^1$ $R^4$ is Me or $-(CH_2)_3-O-(CH_2CH_2O)_x-(CH_2CH(CH_3)O)_y-(CH_2CH_2O)_z-C(O)R^1$, each of x, y, z is an integer ranging from 0 to 20, with the proviso that both $R^3$ and $R^4$ cannot be Me at the same time;

$R^5$ is $-(CH_2)_n-CH_3$;

n is an integer ranging from 1 to 17;

$R^1$ is alkyl having 19 to 37 carbon atoms. and b) a hydroxy compound conforming to the following structure:

R²—OH wherein;

$R^2$ is alkyl having 20 to 38 carbon atoms.

Examples Silicone Compounds

Class 1

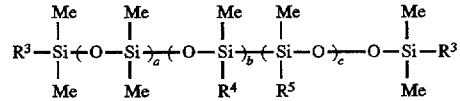

$R^3$ is methyl.

| Example | a | b | c | x | y | z | n |
|---|---|---|---|---|---|---|---|
| 1 | 0 | 1 | 0 | 0 | 10 | 0 | 0 |
| 2 | 100 | 1 | 0 | 10 | 10 | 10 | 0 |
| 3 | 500 | 5 | 0 | 0 | 0 | 0 | 0 |
| 4 | 900 | 4 | 0 | 20 | 20 | 20 | 0 |
| 5 | 2000 | 8 | 0 | 0 | 0 | 0 | 0 |
| 6 | 100 | 10 | 1 | 5 | 2 | 5 | 17 |
| 7 | 200 | 10 | 2 | 1 | 10 | 2 | 11 |
| 8 | 40 | 10 | 3 | 10 | 10 | 0 | 1 |
| 9 | 30 | 4 | 1 | 10 | 20 | 20 | 9 |
| 10 | 50 | 4 | 0 | 5 | 0 | 0 | 0 |
| 11 | 29 | 20 | 3 | 0 | 5 | 0 | 15 |
| 12 | 100 | 15 | 15 | 1 | 5 | 10 | 5 |
| 13 | 20 | 4 | 20 | 10 | 20 | 10 | 3 |
| 14 | 20 | 1 | 0 | 2 | 0 | 0 | 0 |

Class 2

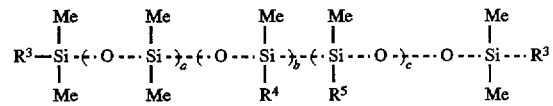

b is 0.

| Example | a | b | c | x | y | z | n |
|---|---|---|---|---|---|---|---|
| 15 | 0 | 0 | 0 | 0 | 10 | 0 | 0 |
| 16 | 100 | 0 | 0 | 10 | 10 | 10 | 0 |
| 17 | 500 | 0 | 0 | 0 | 0 | 0 | 0 |
| 18 | 900 | 0 | 0 | 20 | 20 | 20 | 0 |
| 19 | 2000 | 0 | 0 | 0 | 0 | 0 | 0 |
| 20 | 29 | 0 | 0 | 5 | 2 | 5 | 17 |
| 21 | 50 | 0 | 20 | 1 | 10 | 2 | 11 |
| 22 | 50 | 0 | 1 | 10 | 10 | 0 | 1 |
| 23 | 29 | 0 | 5 | 10 | 20 | 20 | 9 |
| 24 | 50 | 0 | 0 | 2 | 0 | 0 | 0 |
| 25 | 100 | 0 | 3 | 1 | 5 | 0 | 1 |
| 26 | 29 | 0 | 15 | 1 | 5 | 10 | 5 |

Examples Waxes

Example 27 beeswax,

Example 28 candelillia wax

Example 29 carnauba wax

General Procedure

The compounds of the present invention are prepared by the transesterification reaction of the wax and the silicone polymer. The reaction is carried out with a molar ratio of 0.5:1 wax to silicone to 1:0.5 ratio with a preferred mole ratio of 1:1. The wax and the polymer are added to a suitable reaction vessel under agitation. The two are heated to 160–250 C. with a preferred temperature of between 180–200 C. An esterification catalyst selected from para toluene sulfonic acid, tin oxylate, sulfuric acid and other esterification catalysts. The reaction is conducted at 180 to 200 C. for three to eight hours. During that time alkyl alcohol is generated. This alcohol has found to be a critical element to the composition's functionality. It's presence allows for better coupling of the product when put in formulations. Specifically, the alcohol, and the silicone ester together make up a coupling composition which allows for the compatabilization of oil phases and silicone phases which are normally incompatible.

EXAMPLE 30

To 2914.3 grams of silicone polymer (example 1) is added 606.8 grams of the specified wax (example 27). Next tin oxylate is added 0.1% by weight, based upon the total number of grams of total reaction mass. The reaction mass is heated to 200 C., and held for 3–6 hours. The resulting composition is used as prepared without additional purification.

EXAMPLE 31–110

Example 30 is repeated, only this time the specified amount of the specified silicone polymer replaces the prior silicone polymer and the specified wax and quantity of wax replaces the wax specified in Example 30.

| | Silicone | | Wax | |
|---|---|---|---|---|
| Example | Example | Grams | Example | Grams |
| 31 | 1 | 707.0 | 27 | 100.0 |
| 32 | 2 | 10487.0 | 27 | 1254.0 |
| 33 | 3 | 9017.0 | 27 | 3526.0 |
| 34 | 4 | 23082.2 | 27 | 1340.0 |
| 35 | 5 | 12367.0 | 27 | 1236.7 |
| 36 | 6 | 1574.0 | 27 | 300.8 |
| 37 | 7 | 2636.7 | 27 | 500.7 |

-continued

| Example | Silicone Example | Grams | Wax Example | Grams |
|---|---|---|---|---|
| 38 | 8 | 1580.6 | 27 | 1580.0 |
| 39 | 9 | 3306.2 | 27 | 690.0 |
| 40 | 10 | 1449.1 | 27 | 750.9 |
| 41 | 11 | 554.0 | 27 | 500.0 |
| 42 | 12 | 1789.2 | 27 | 400.8 |
| 43 | 13 | 3067.1 | 27 | 667.9 |
| 44 | 14 | 2205.8 | 27 | 689.0 |
| 45 | 15 | 578.0 | 27 | 120.0 |
| 46 | 16 | 5206.9 | 27 | 520.6 |
| 47 | 17 | 22898.0 | 27 | 2289.8 |
| 48 | 18 | 6203.9 | 27 | 3101.5 |
| 49 | 19 | 91198.1 | 27 | 911.9 |
| 50 | 20 | 1735.4 | 27 | 357.9 |
| 51 | 21 | 6288.0 | 27 | 928.8 |
| 52 | 22 | 3344.1 | 27 | 668.5 |
| 53 | 23 | 2750.1 | 27 | 600.8 |
| 54 | 24 | 4483.1 | 27 | 897.9 |
| 55 | 25 | 5207.9 | 27 | 520.8 |
| 56 | 26 | 2914.2 | 27 | 600.9 |
| 57 | 1 | 707.0 | 27 | 79.7 |
| 58 | 25 | 5207.9 | 27 | 1234.4 |
| 59 | 26 | 2914.2 | 27 | 508.9 |
| 60 | 1 | 707.0 | 28 | 707.0 |
| 61 | 2 | 10487.0 | 28 | 546.7 |
| 62 | 3 | 9017.0 | 28 | 606.9 |
| 63 | 4 | 23082.2 | 28 | 13153. |
| 64 | 5 | 12367.0 | 28 | 2461.7 |
| 65 | 6 | 1574.0 | 28 | 157.4 |
| 66 | 7 | 2636.7 | 28 | 515.8 |
| 67 | 8 | 1580.6 | 28 | 158.0 |
| 68 | 9 | 3306.2 | 28 | 661.2 |
| 69 | 10 | 1449.1 | 28 | 288.9 |
| 70 | 11 | 554.0 | 28 | 554.0 |
| 71 | 12 | 1789.2 | 28 | 350.8 |
| 72 | 13 | 3067.1 | 28 | 612.7 |
| 73 | 14 | 2205.8 | 28 | 440.8 |
| 74 | 15 | 578.1 | 28 | 571.0 |
| 75 | 16 | 5026.1 | 28 | 1023.5 |
| 76 | 17 | 22898.4 | 28 | 11445.0 |
| 77 | 18 | 6203.4 | 28 | 1234.6 |
| 78 | 19 | 91198.3 | 28 | 4567.0 |
| 79 | 20 | 1735.1 | 28 | 290.7 |
| 80 | 21 | 6288.0 | 28 | 350.9 |
| 81 | 22 | 3344.1 | 28 | 668.7 |
| 82 | 23 | 2750.1 | 28 | 599.9 |
| 83 | 24 | 4483.1 | 28 | 910.2 |
| 84 | 25 | 5207.2 | 28 | 1056.8 |
| 85 | 26 | 2914.1 | 28 | 606.3 |
| 86 | 1 | 707.0 | 29 | 95.6 |
| 87 | 2 | 10487.0 | 29 | 2154.7 |
| 88 | 3 | 9017.0 | 29 | 2345.5 |
| 89 | 4 | 23082.2 | 29 | 11231.4 |
| 90 | 5 | 12367.0 | 29 | 1836.7 |
| 91 | 6 | 1574.0 | 29 | 300.2 |
| 92 | 7 | 2636.7 | 29 | 456.7 |
| 93 | 8 | 1580.6 | 29 | 300.5 |
| 94 | 9 | 3306.2 | 29 | 661.7 |
| 95 | 10 | 1449.1 | 29 | 290.8 |
| 96 | 11 | 554.0 | 29 | 105.6 |
| 97 | 12 | 1789.2 | 29 | 359.9 |
| 98 | 13 | 3067.1 | 29 | 612.3 |
| 99 | 14 | 2205.8 | 29 | 220.5 |
| 100 | 15 | 578.1 | 29 | 100.7 |
| 101 | 16 | 5026.2 | 29 | 1040.0 |
| 102 | 17 | 22898.0 | 29 | 1144.0 |
| 103 | 18 | 6203.3 | 29 | 620.3 |
| 104 | 19 | 91198.1 | 29 | 9119.8 |
| 105 | 20 | 1735.4 | 29 | 350.9 |
| 106 | 21 | 6288.3 | 29 | 1234.5 |
| 106 | 22 | 3344.1 | 29 | 675.6 |
| 108 | 23 | 2750.1 | 29 | 275.0 |
| 109 | 24 | 4483.2 | 29 | 8916.1 |
| 110 | 25 | 5207.8 | 29 | 1234.5 |
| 111 | 26 | 2914.3 | 29 | 606.8 |

APPLICATIONS EXAMPLES

Lipsticks

The compositions of the invention can be used to make lipsticks, which comprise:

a) 1–70% of a volatile solvent;

b) 0.1–15% silicone ester of the current invention, c) 10–45% wax;

d) 5–50% powder.

The composition of the invention when used in a lipstick using the formulation above exhibit superior transfer resistance and overcomes problems encountered when products are made without using the compositions of the present invention.

(1) Lipsticks are solids and as such stick intergerity and uniformity is very important. Because there are many solid products in these compositions, each having a variety of melting points and firmness as well as differing solubilities in each other, a phenomenon known as syneresis occurs. Syneresis is a tendency of the solid lipstick to ooze oil and crack. Syneresis effects spreadability and other esthetics, and is highly undesirable. The outstanding coupling properties of the compounds of the present invention overcome the syneresis problem when used at a level of 0.1–15%. The compounds of the present invention couple the silicone and the waxes in a uniform stick.

(2) Lipsticks have a tendency to peel off the lips with time. This relates to the plasticizing of the product and the elastomeric properties of the film so deposited. The compounds of the present invention provide a film which is more flexible and consequently does not peel off.

(3) Lipsticks have a tendency to have a matte rather than high gloss finish. The compounds of the present invention are glossy.

We have, therefore, surprisingly and unexpectedly found that the use of the compounds of the present invention overcomes all of these problems.

What is claimed:

1. A composition comprises:

a) a silicone ester conforming to the following structure

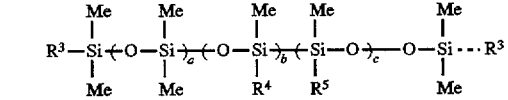

wherein:

Me is methyl;

a is an integer ranging from 0 to 2000;

b is an integer ranging from 1 to 20;

c is an integer ranging from 0 to 20;

$R^3$ is Me or $-(CH_2)_3-O-(CH_2CH_2O)_x-(CH_2CH(CH_3)O)_y-(CH_2CH_2O)_z-C(O)R^1$ $R^4$ is Me or $-(CH_2)_3-O-(CH_2CH_2O)_x-(CH_2CH(CH_3)O)_y-(CH_2CH_2O)_z-C(O)R^1$, each of x, y, z is an integer ranging from 0 to 20, with the proviso that both $R^3$ and $R^4$ cannot be Me at the same time;

$R^5$ is $-(CH_2)_n-CH_3$;

n is an integer ranging from 1 to 17;

$R^1$ is alkyl having 19 to 37 carbon atoms; and b) a hydroxy compound conforming to the following structure:

$R^2-OH$ wherein;

$R^2$ is alkyl having 20 to 38 carbon atoms.

2. A composition of claim 1, wherein the concentration of the hydroxy compound ranges from 1 to 10% by weight.

3. A composition of claim 1 wherein the concentration of the hydroxy compound ranges from 5 to 10% by weight.

4. A composition of claim 1 wherein n is an integer ranging from 11 to 17.

5. A composition of claim 1 wherein a is an integer ranging from 10 to 50.

6. A composition of claim 1 wherein a is an integer ranging from 15 to 25.

7. A composition of claim 1 wherein c is 0.

8. A composition of claim 1 wherein c is an integer ranging from 1 to 10.

9. A composition of claim 1 wherein c is an integer ranging from 1 to 5.

10. A composition made by the esterification reaction of a silicone compound conforming to the following structure:

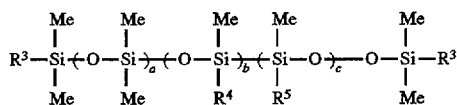

wherein:

Me is methyl;

a is an integer ranging from 0 to 2000;

b is an integer ranging from 1 to 20;

c is an integer ranging from 0 to 20;

$R^3$ is Me or $-(CH_2)_3-O-(CH_2CH_2O)_x-(CH_2CH(CH_3)O)_y-(CH_2CH_2O)_z-H$ $R^4$ is Me or $-(CH_2)_3-O-(CH_2CH_2O)_x-(CH_2CH(CH_3)O)_y-(CH_2CH_2O)_z-H$, each of x, y, z is an integer ranging from 0 to 20, with the proviso that both $R^3$ and $R^4$ cannot be Me at the same time;

$R^5$ is $-(CH_2)_n-CH_3$;

n is an integer ranging from 1 to 17; and a wax selected from the group consisting of beeswax, carnauba wax and candelillia wax.

11. A composition of claim 10, wherein said wax is beeswax.

12. A composition of claim 10, wherein said wax is carnauba wax.

13. A composition of claim 10, wherein said wax is candelillia wax.

14. A composition of claim 10, wherein said reaction is carried out at a temperature of between 180 and 200 C.

* * * * *